United States Patent [19]

Dahms

[11] Patent Number: 4,786,602
[45] Date of Patent: Nov. 22, 1988

[54] METHOD FOR COLORIMETRIC ANALYSIS OF WATER CONTENT

[76] Inventor: Harald Dahms, 472 Madison Ave., Toms River, N.J. 08753

[21] Appl. No.: 863,602

[22] Filed: May 15, 1986

[51] Int. Cl.$^4$ ............................................. G01N 33/18
[52] U.S. Cl. ....................................... 436/42; 436/171
[58] Field of Search .................................. 436/42, 171

[56] References Cited

U.S. PATENT DOCUMENTS

| | | | |
|---|---|---|---|
| 4,005,983 | 2/1977 | Dahms | 436/42 |
| 4,211,614 | 7/1980 | Eppstein et al. | 436/42 X |
| 4,536,369 | 8/1985 | Sakurada et al. | 422/65 |

*Primary Examiner*—Barry S. Richman
*Assistant Examiner*—Jill Johnston

[57] ABSTRACT

A method for the colorimetric determination of water content of an unknown sample, using the Karl Fischer reaction. The Karl Fischer reagent in a container has added to it a dye whose optical absorption preferably does not overlap with the optical absorption of the Karl Fischer reagent. Measurement of the optical absorption of the reagent/dye mixture is then made at two wavelengths, one wavelength being strongly absorbed by iodine in the reagent while the other wavelength is strongly absorbed by the dye. After the unknown sample is added, optical absorption measurements are again made at the two wavelengths. The measurements made at the wavelength where the dye strongly absorbs are used to correct the optical absorption measurements made at the wavelength where iodine strongly absorbs. This corrects for all factors affecting optical density other than the amount of water in the unknown sample.

21 Claims, No Drawings

METHOD FOR COLORIMETRIC ANALYSIS OF WATER CONTENT

DESCRIPTION

1. Field of the Invention

This invention relates to a method for the colorimetric determination of water content of a sample using Karl Fischer reagents contained in vials, and more particularly to measurement of the optical density of solutions in these vials using two different wavelengths.

2. Background Art

The determination of water content is important in many commercial products. For example, minute quantitites of water in chemical process streams are detrimental for certain reactions. Further, the electrical properties of insulators are strongly dependent on water traces, and the water content of fluids such as gasoline has to be kept below a certain level. From these few examples, it is apparent that water determinations are among the most frequently performed analyses in many laboratories.

The currently most widely practiced water determination is the "Karl Fischer" method, named after its originator Karl Fischer who described the basis of this method in "Zeitschrift Fuer Angwandte Chemie", Vol. 48, pages 394–396 (1935). In this method, the sample containing an unknown amount of water is added to a Karl Fischer reagent, hereinafter denoted K. F. reagent. This reagent is usually a solution of iodine and sulfur dioxide in pyridine and methanol or other solvents. Pyridine-free solutions are well known in the art, also.

Due to the presence of iodine in the K. F. reagent, its color is brown. When an unknown sample containing water is added to the K. F. reagent, the iodine is consumed so that the dark brown color of the iodine in the "fresh" reagent disappears, changing to a light yellow color of the "spent" reagent. In a typical water determination by the Karl Fischer method, a water containing sample is injected into a prepacked volume of the K. F. reagent and the change in optical absorbance of the K. F. reagent is measured. The change in optical absorbance can be transofrmed by an electrical circuit into a direct readout of water content of the sample. This technique gives immediate quantitative results irrespective of the fading of strength of the K. F. reagent during storage. Further details of this technique, which measures a change in optical absorbance, can be obtained by referring to my U.S. Pat. No. 4,005,983. in that patent, electrical compensation in the associated circuitry is used to adjust a zero-set scale in order to correct for dilution when the sample is introduced.

While the general technique described in my aformentioned patent has proved to be useful, there is some need for obtaining a higher accuracy in the reading. If higher accuracy can be obtained, this will also result in higher sensitivity so that samples with very small water content, for example in the low parts per million range, can be reliably and accurately analyzed. Present limitations in the optical absorbance technique described hereinabove relate to the containers that are used, the unknown properties of the added sample, and the inaccuracies produced by the use of these glass containers. For example, the glass walls of the containers in which the K. F. reagent-sample reaction occurs are not optically perfect. This means that the second optical reading, after the addition of the unknown sample and reinsertion of the container into the optical instrument, is changed by the difference in properties in the glass walls of the containers. A further factor affecting the measurement accuracy is that the optical properties of the added unknown sample such as its optical density, refractive index, etc., are unknown and change the second optical absorbance reading, thereby rendering it inaccurate. Another factor which impairs the accuracy of this technique is that the containers are generally cylindrical glass vessels. Optical readings through these vessels are more complex than through perfectly rectanglular optical containers, and the readings are further complicated by the addition of the unknown optical properties of the added sample.

Accordingly, it is a primary object of the present invention to provide a technique and apparatus therefor that will improve the reliability of the optical absorbance method for the colorimetric determination of water content of a sample.

It is another object of this invention to provide a K. F. method for water determination of a sample using colorimetric determination techniques which compensate for the accuracy-limiting factors described hereinabove.

It is another object of the present invention to provide an improved colorimetric technique for determination of water content of a sample, where the improved technique is simple and can be accomplished by the use of straightforward equipment.

It is a further object of the present invention to provide an improved technique for determining the water content of a sample by colorimetric methods wherein a more accurate and reliable determination is made.

It is another object of the present invention to provide a technique for the colorimetric determination of water content of a sample wherein increased sensitivity results.

It is another object of this invention to provide an improved technique for the determination of water content of a sample, wherein colorimetric determinations can be made of samples having extremely small water content.

DISCLOSURE OF THE INVENTION

In the technique of this invention, the water containing sample is added to a prepacked volume of K. F. reagent and a change in optical absorbance of K. F. reagent is measured. However, the difference over the technique described in U.S. Pat. No. 4,005,983 is that in the present invention a small amount of dye solution is present in the K. F. reagent in the container. This dye has its maximum absorption at a wavelength which is different than the wavelengths that are optically absorbed by iodine. Optical absorption measurements are made on the solution including both the K. F. reagent and the dye at two different wavelengths. The two wavelengths are chosen such that at a first wavelength the light is absorbed more strongly by the iodine, while at a second wavelength the light is more strongly absorbed by the dye.

The unknown sample whose water content is to be determined is then added to the K. F. reagent-dye solution. After mixing, the solution is again measured at the same two wavelengths. As in U.S. Pat. No. 4,005,983, the change of optical density at the first wavelength (where iodine absorbs light more strongly) is essentially a measure of the water content of the sample. However, the change in optical density at the second wavelength (a wavelength where the dye absorption is strongest) is used as a correction for the reading at the first wavelength. This provides for extremely accurate and reliable measurements even if the water content of the sample is extremely small.

These and other objects, features, and advantages will be apparent from the following more particular description of the preferred embodiments.

BEST MODE FOR CARRYING OUT THE INVENTION

In the practice of this invention, a very reliable and accurate measurement of the water content of an unknown sample is made by using two wavelengths when making the measurement. The first wavelength is one which is readily absorbed by iodine and in this way is a direct indication of the water content of the unknown sample, since the amount of iodine in the K. F. reagent is affected by the amount of water present in the unknown sample. However, in order to give more accuracy to that determination, a dye is added to the K. F. reagent and a second wavelength is used which is strongly absorbed by the dye. After the sample is added to the K. F. reagent, and radiation of the second wavelength is again applied, an optical density measurement will be obtained which will depend upon the optical properties of the system, the dilution effect when the sample is added, and the optical properties introduced by the unknown sample. This measurement at the second wavelength corrects for all factors other than the amount of water in the unknown sample, and therefore provides excellent accuracy even if the amount of water in the unknwon sample is extremely small.

Thus, in this invention, the K. F. reagent in the sample has a dye added to it before any colorimetric determinations are made. Prior to the addition of the unknown sample, radiation of a first wavelength (strongly absorbed by iodine) is directed through the K. F. reagent/dye mixture. The dye has maximum absorption at a wavelength different than this first wavelength. Thus, this first wavelength is used to directly measure the amount of iodine in the K. F. reagent. Prior to adding the unknown sample, radiation of a second wavelength (which is strongly absorbed by the dye) is directed through the K. F. reagent/dye mixture. This second wavelength is readily absorbed by the dye and is used for indicating changes due to dilution effects, optical properties of the unknown sample, and the optical properties of the container and system used for these measurements.

The unknown sample is then added to the K. F. reagent/dye mixture. After further mixing, the K. F. reagent/dye/sample mixture is measured at these two wavelengths. The change in optical density at the first wavelength (where the iodine strongly absorbs) is an indication of the water content of the sample. The change in optical density at the second wavelength (the dye absorption wavelength) is an indication of the correction to be applied to the optical density measurement made at the first wavelength.

The following is a more detailed description of the correction to be applied in this two-wavelength method for determining water content. The amount $a_w$ of water in the sample is determined in accordance with the following expression:

$$a_w = \frac{1}{k}\left(A_1 \frac{A_{02}}{A_2} - A_{01}\right)$$

where:

$A_{01}$ is the optical absorbance of the reagent/dye mixture at the first wavelength (iodine absorption), prior to adding the sample.

$A_1$ is the optical absorbance of the reagent/dye/sample mixture at the first wavelength (iodine absorption), after adding the sample.

$A_{02}$ is the optical absorbance of the reagent/dye mixture at the second wavelength (dye absorption), prior to adding the sample.

$A_2$ is the optical absorbance of the reagent/dye/sample mixture at the second wavelength (dye absorption), after adding the sample.

$a_w$ is the amount of water in the sample, in micrograms.

$$k = \frac{\Delta A_1}{a_w} = \text{change of optical absorbance when adding}$$

In operation, the vial is inserted into the optical instrument and the absorbances $A_{01}$ and $A_{02}$ are measured. The sample to be analyzed is then injected into the vial and the contents are mixed. The absorbances $A_1$ and $A_2$ are then measured. The quantity k is a constant which had been determined previously, and remains the same for all measurements. The amount of water is then calculated, using the expression above.

These calculations do not have to be performed manually, but instead can be programmed directly into the instrument so that all computations are performed automatically.

It has been found that this two-wavelength measurement technique gives significantly improved results over conventional one-wavelength techniques. Further, the principles of this invention may be extended and used for more complex correction methods.

This technique will be more apparent by consideration of the following example.

EXAMPLE

A Diagnostest computer colorimeter, as sold by Diagnostics Division of DOW Chemical Company, was used. The containers holding the K. F. reagent and the dye were disposable culture tubes made by Corning under Catalog No. 99447. These containers were closed with Teflon TM -lined screw caps. The containers were filled with seven milliliters of a dilute solution of K. F. reagent (Harleco Co., Catalog No. 3786), which was diluted with a mixture of 80% chloroform and 20% methanol. The optical density of the K. F. reagent at 420 nm (nanometers) was about 0.75 (iodine absorbs strongly at 420 nm).

The solution in the container also contained as a dye a small amount of Brilliant Blue G (Sigma Co., Cat. No. B-1131). The absorption of this K. F. reagent/dye mixture at 660 nm was about 0.6. A large number (about 50) of these tubes were prepared and tested with samples containing small amounts of water (typically containing about 50 ppm of water. The optical density of the solution in these tubes was measured at 420 nm in order to determine the iodine absorption, and also at 660 nm to measure the dye absorption.

The unknown sample containing water was then added by piercing the Teflon TM lining of the vials with a hypodermic syringe containing the sample. The optical densities at the two wavelengths (420 and 660 nm) were again measured. The optical densities measured at the dye absorption wavelength (660 nm) were used to correct for the optical density measurements at the iodine absorption wavelength (420 nm).

For all determinations, the actual water content, determined by an independent coulometric method, was closer to the result obtained by the improved method, i.e., closer to the result obtained when the dye correction factor was utilized. In this improved method, the decrease of optical density due to iodine consumption, i.e., due to the K. F. reaction $$I_2 + H_2O + SO_2 = 2HI + SO_3$$

at the first wavelength (420 nm) is corrected by the decrease in optical density at the second wavelength (the inert dye absorption at 660 nm).

It is believed that the foregoing technique is the first use of a dye in this particular manner to correct for optical inaccuracies when measuring the water content of an unknown sample. It is noted, however, that dyes have been used in optical measurements in the past, as can be seen by referring to, for instance, my U.S. Pat. No. 3,723,062. In that patent, the detection of end points in a colorimetric titration is obtained through the use of a dye. A dual wavelength photodetector system and an indicator substance (dye) in the titration solution are used. The indicator has a different light absorption characteristic in each of its states and for this reason two wavelengths are chosen. One wavelength is absorbed when the indicator is in a first state while the other wavelength is absorbed when the indicator is in its second state. Thus, the two wavelengths are used to detect the various states of the same material, i.e., the indicator.

The foregoing is in contrast with the present invention where the dye does not change state and wherein the dye is chosen to be inert in the mixture so that it does not enter into the K. F. reaction and also does not react with any of the ingredients of the mixture. In the present invention, the dye is used to render more accurate a measurement made at a first wavelength, where the first wavelength is chosen to be a precise indicator of iodine content (which is itself directly dependent upon the water content of the unknown sample).

As noted previously, the dye should be perfectly inert and not enter into a reaction with either the K. F. reagent or the unknown sample in a way to affect the customary K. F. reaction. This insures that the change in iodine amount is directly related to the change in water content and that the dye change in optical absorbance is totally related to all other factors, including the effect of the surfaces of the vials, the optical properties of both the K. F. reagent and the unknown sample, dilution effects, and all other factors which may in some way modify the optical absorbance measured at the wavelength of absorption of iodine.

It is also important to have no overlap, or minimal overlap, between the optical absorption of the dye and the optical absorption of iodine at the wavelengths selected for measuring optical density. This assures that the change in optical absorbance at the first wavelength (where iodine absorbs) is totally or at least substantially due to the water content of the unknown sample, while the change in optical absorbance of the dye at the second wavelength (where the dye absorbs) is due only to all other optical effects, as noted above. If there is an overlap of the optical absorptions for the dye and the iodine at the wavelengths chosen, confusion will result as to what has caused the change in optical absorbance. For example, if a 10% overlap in optical absorption is assumed, a question arises as to whether the dye is changing its optical absorbance due to the addition of water or due to the optical effects for which it is chosen to compensate.

While it is preferable that both the iodine and the dye do not absorb at the chosen wavelengths for measurement, some degree of overlap of absorption can be tolerated. If there is to be any overlap in the optical absorption of iodine and the dye, it is preferable that it be at only one of the wavelengths chosen for the measurement. If there is an overlap in the optical absorptions of iodine and the dye at both of the wavelengths chosen for the measurement, then the overlap should be less than about 25% at each of these wavelengths. However, if there is overlap of optical absorption of iodine and the dye at only one of the wavelengths used for measurement, this technique will provide good correction of the optical measurement if there is an overlap of less than about 50%.

Thus, the effect of an overlap in absorption of iodine and the dye at either of the wavelengths used for measurement introduces ambiguities in the measurements themselves. The question becomes whether the dye has changed or whether the iodine level has changed when there is an overlap in the optical absorption spectrum. Of course, further tests can be undertaken to determine the relative percentage ranges of change of optical absorption of iodine and the dye if there is overlap at the measurement wavelengths. These relative percentage changes can be factored into the instrumentation used for correction in order to provide a reliable and accurate water content determination.

In the present invention, the dye is used to provide correction of an optical absorbance measurement that is in turn used to indicate the water content. The dye is not intended to be an indicator of the state of the sample or a substitute for the sample itself. It is intended that the dye be totally inert and not enter into any of the reactions used to determine water content by the Karl Fischer reaction, or in any way react with any of the components of the solution in the container. In this way, the technique of the present invention further distinguishes from the technique of aforementioned U.S. Pat. No. 3,723,062, where the dye in that invention was actually a substitute for the sample.

As is apparent from the foregoing examples, the amount of the dye which is used is determined by practical effects. For example, large quantities of dyes generally are not used as they will make the sample very dark and affect to a large extent the optical absorbance. Dilute solutions of dyes are best where the absorption of the K. F. reagent/dye mixture is less than 1. Generally, the amount of the dye chosen is such that the peak absorption of the dye at the second wavelength is approximately the same as the amount of absorption of iodine at the first wavelength. That is, the dye absorption and the iodine absorption have about the same intensity range.

It will be obvious to those of skill in the art that there are numerous ways to perform the inventive method automatically and to apply the necessary correction in optical density by electronic circuitry. Further, it is known in the art how to store the optical densities at both wavelengths before and after addition of the sample, and to perform all functions automatically so that the user would see only the final result, which is the amount of water present in the unknown sample. Reference is made to each of the aforementioned U.S. Pat. Nos. 3,723,062 and 4,005,983 for representative apparatus that provides an automatic readout of the final desired result.

As described previously, the nature and quality of the container vial affects the accuracy of the water determination. In order to be able to use mass-produced disposable tubes as container vials, it is herein recognized that such tubes are not optically perfect and uniform. Therefore, it is helpful to always insert such tubes in the same position and orientation for the two measurements at the first and second wavelengths. In order to do so accurately, the cap of the tube can be fitted with an "arm" which is used as an alignment pin. By the use of such a mechanism, the tube is aligned in an identical manner for the two wavelength measurements that occur prior to insertion of the unknown example, and after the insertion of the unknown sample. Other means of fitting the vial with an eccentric member, each as of permanently attaching a piece of rod, are quite apparent.

It is understood that the present method is not limited to vials and that other vessels, such as small glass bottles, may be used.

It is also understood that more than one unknown sample may be analyzed in the same vessel. After the first sample has been analyzed according to the method described above, the final optical measurements ($A_1$ and $A_2$) are now used as starting optical measurements for the next determination, i.e., they are used as $A_{01}$ and $A_{02}$ for the analysis of the second sample. This sequence may be repeated with subsequent samples until the iodine in the glass vessel is used up by reaction with water in the samples, or the vessel is filled with sample, whichever comes first.

In the practice of this invention, a technique is described for the determination of water content in an unknown sample by a colorimetric method in which improved reliability and accuracy are obtained, regardless of the amount of water present in the unknown sample. Thus, it will be apparent that variations can be made therein which are consistent with the principles described hereinabove. As an example, the choice of dye can be varied but it is important to have the dye inert so that it will not take part in any of the reactions and will not react with any of the components of the vessel solution. In particular, it is preferable that the dye not be attacked by iodine over a period of time so that the dye color doesn't change. This would affect the lifetime of the sample and the wavelength range of its absorption. Of course, it may be possible to compensate for certain effects, although that type of operation is undesireable in many practical instruments.

Those of skill in the art will also recognize that variations, such as changing the applied wavelengths, can be made without altering the context of the present invention.

Having thus described my invention, what I claim as new and desire to secure by Letters Patent is:

1. A method of colorimetric determination of water content of a sample by a Karl Fischer type reaction, comprising the steps of:

measuring the optical density of a volume of an iodine-containing Karl Fischer reagent and dye mixture at a first wavelength and a second wavelength, said first wavelength being more strongly absorbed by iodine and said second wavelength being more strongly absorbed by said dye, adding a sample to the volume of iodine-containing Karl Fischer reagent and dye mixture, the sample and the iodine-containing Karl Fischer reagent reacting in accordance with a Karl Fischer type reaction to alter the amount of iodine contained in said volume, measuring the optical density of the volume of the iodine-containing Karl Fischer reagent, dye, and sample at said first wavelength and said second wavelength, the change in optical density at said first wavelength being directly related to the amount of water in the sample, and determining the amount of water in the sample using the change in optical density at said second wavelength to correct the change in optical density measured at said first wavelength.

2. The method of claim 1, where the Karl Fischer reagent and the dye are present in a vial that is transparent to said first wavelength and said second wavelength.

3. The method of claim 1, where the dye is substantially inert with respect to the Karl Fischer reagent and the sample.

4. The method of claim 1, where the sample is a solid.

5. The method of claim 1, where the sample is a liquid.

6. The method of claim 1, where the sample is a gas.

7. The method of claim 1, where the dye is Brilliant Blue, and said second wavelength is approximately 660 nm.

8. The method of claim 7, where said first wavelength is about 420 nm.

9. The method of claim 1, where the Karl Fischer reagent and the dye have optical absorbances versus wavelengths which do not substantially overlap with one another.

10. The method of claim 9, where the amount of overlap of optical absorbances of iodine and the dye is less than about 50% at either of said first wavelength or said second wavelength.

11. The method of claim 9, where the amount of overlap of optical absorbances of the Karl Fischer reagent and the dye is less than about 25% when the optical absorbances of iodine and the dye overlap at both said first wavelength and said second wavelength.

12. A method for determining water content of an unknown sample by the Karl Fischer method, using the steps of:

measuring the optical density of a known volume of an iodione-containing Karl Fischer reagent and a dye at a first wavelength at which iodine strongly absorbs while the dye absorbs at most, only minimally, measuring the optical density of said known volume at a second wavelength at which the dye strongly absorbs while iodine absorbs at most, only minimally, adding the sample to said known volume to create a new volume of iodine-containing Karl Fischer reagent, dye, and sample, the sample reacting with the iodine-containing reagent in accordance with a Karl Fischer type reaction, measuring the optical density of said new volume of iodine-containing reagent, dye, and sample at said first wavelength, the change in optical density at first wavelength, the change in optical density at said first wavelength being related to the amount of water in the sample, measuring the optical density of said new volume of iodine-containing reagent, dye, and sample at said second wavelength, the change in optical density at said second wavelength being a correction to the change in optical density at said first wavelength, and determining the water content of the sample by applying said correction to the change in optical density at said first wavelength.

13. The method of claim 12, where the iodine containing Karl Fischer reagent and the dye are placed in a vial having an alignment member thereon to ensure the same orientation of the vial during the measuring steps.

14. The method of claim 12, where the dye is substantially inert with respect to the iodine containing Karl Fischer reagent and the sample.

15. The method of claim 12, where said first wavelength is about 420 nm.

16. The method of claim 12, where the optical absorbance of iodine and the optical absorbance of the dye do not substnatially overlap at said first wavelength and said second wavelength.

17. The method of claim 16, where the amount of overlap of optical absorbances of iodine and the dye at either said first wavelength or said second wavelength is less than about 50%.

18. The method of claim 16, where there is overlap in the optical absorbances of iodine and the dye at both said first wavelength and said second wavelength, the amount of overlap being less than about 25% at said first wavelength and said second wavelength.

19. The method of claim 12, where the dye is Brilliant Blue.

20. The method of claim 19, where said second wavelength is about 660 nm.

21. The method of claim 20, where said first wavelength is approximately 420 nm.

* * * * *